United States Patent [19]

Hallcher et al.

[11] 4,072,583

[45] Feb. 7, 1978

[54] ELECTROLYTIC CARBOXYLATION OF CARBON ACIDS VIA ELECTROGENERATED BASES

[75] Inventors: Richard C. Hallcher, Bridgeton; Manuel M. Baizer, St. Louis; Donald A. White, Creve Coeur, all of Mo.

[73] Assignee: Monsanto Company, St. Louis, Mo.

[21] Appl. No.: 730,553

[22] Filed: Oct. 7, 1976

[51] Int. Cl.$^2$ ............................ C25B 3/00; C25B 3/10
[52] U.S. Cl. ...................................... 204/59 R; 204/72
[58] Field of Search ...................... 204/59 R, 72, 73 R

[56] References Cited

U.S. PATENT DOCUMENTS

| 3,032,489 | 5/1962 | Loveland | 204/73 R |
| 3,344,045 | 9/1967 | Neikam | 204/59 R |
| 3,864,225 | 2/1975 | Tyssee | 204/59 R |
| 3,945,896 | 3/1976 | Tyssee | 204/59 R |
| 4,013,524 | 3/1977 | Tyssee | 204/59 R |
| 4,028,201 | 6/1977 | Tyssee | 204/72 |

*Primary Examiner*—F.C. Edmundson
*Attorney, Agent, or Firm*—Wendell W. Brooks; James W. Williams, Jr.; Joseph D. Kennedy

[57] ABSTRACT

Electrolytic carboxylation of carbon acids via electrogenerated bases leads to carboxylated carbon acids.

38 Claims, No Drawings

ELECTROLYTIC CARBOXYLATION OF CARBON ACIDS VIA ELECTROGENERATED BASES

BACKGROUND OF THE INVENTION

This invention relates to the electrolytic carboxylation of carbon acids and in particular to the use of electrogenerated bases as catalysts for the preparation of carboxylated carbon acids.

Electrochemical reduction of organic compounds often affords strongly basic and/or nucleophilic species, for example, carbanions, radical anions, dianions, and the like. The nucleophilic character of these species has been extensively exploited in many coupling, polymerization, and displacement reactions as reported in *Organic Electrochemistry* (Baizer, ed.) Marcel Dekker, New York, pp. 679-704; 947-974 and Baizer et al, *Journal of Organic Chemistry*, 37, 1951 (1972). However, their basicity has been used in synthesis only to a limited extent. For example, the synthetic utilization of electrogenerated bases in the Wittig reaction, the Stevens rearrangement, and the Michael addition reaction has been described, respectively, in Iversen et al, *Tetrahedron Letters*, 3523 (1969); Iversen, *Tetrahedron Letters*, 55 (1971); and Baizer et al, *Tetrahedron Letters*, 5209 (1973).

The progress of synthetic utilization of electrogenerated bases has been impeded by the usual requirement that the electrogenerated base must be present in stoichiometric amounts, an unappealingly wasteful and expensive requirement. And even in these reactions where the electrogenerated base need be present in only catalytic amounts, for example, the Michael addition reaction noted hereinabove, the utility of such bases has been severely limited in that little, if any, advantage is demonstrated over corresponding chemical procedures.

Furthermore, processes employing electrogenerated bases in carboxylation reactions have been glaringly unavailable, possibly because of the general expectation that such bases would successfully compete for the available in situ carbon dioxide with the anionic species which it is desired to carboxylate.

The difficulties and disadvantages encountered in the prior art processes of synthetic utilization of electrogenerated bases are overcome by the discovery that the electrolytic carboxylation of carbon acids is conveniently accomplished via electrogenerated bases to yield carboxylated carbon acids.

SUMMARY OF THE INVENTION

According to the present invention, it has been discovered that the electrolytic carboxylation of carbon acids is conveniently accomplished via electrogenerated bases in anhydrous aprotic solvents to yield carboxylated carbon acids.

The carboxylated carbon acid products obtained in the present process can be recovered by any of a number of wellknown procedures as the free carboxylic acid, salts, and esters thereof.

DETAILED DESCRIPTION OF THE INVENTION

Electrolytic carboxylation of carbon acids via electrogenerated bases leads to carboxylated carbon acids.

In accordance with the present process, a direct electric current is passed through an anhydrous aprotic liquid electrolysis medium comprising such carbon acid, a base precursor, an anhydrous aprotic solvent, added carbon dioxide, and supporting electrolyte. It is suggested that the process comprise:

(a) electrogenerating a base from the base precursor;

(b) allowing the electrogenerated base to react with the carbon acid to abstract at least one proton and produce a carbon acid anion and the conjugate acid of the electrogenerated base;

(c) allowing the carbon acid anion to react with the added carbon dioxide to form a carboxylated carbon acid; and (d) recovering the carboxylated carbon acid.

Equations (1), and (2), and (3) illustrate the general reactions involved $$BP \xrightarrow{Reduction} EGB^- \qquad (1)$$

$$EGB^- + RH \rightarrow EGBH + R^- \qquad (2)$$

$$R^- + CO_2 \rightarrow RCOO^- \qquad (3)$$

wherein BP is a base precursor; $EGB^-$ is an electrogenerated base; RH is a carbon acid of sufficiently low $pK_a$ (high acid strength) to permit or allow abstraction of a proton by the electrogenerated base; $R^-$ is the carbon acid anion or conjugate base of the carbon acid; EGBH is the conjugate acid of the electrogenerated base; and $RCOO^-$ is a carboxylated carbon acid.

From a practical viewpoint, it is advantageous that the conjugate acid of the electrogenerated base is capable of being readily reoxidized to the base precursor. Under such circumstances and conditions, the base precursor and the electrogenerated base derived from it will become involved as catalysts. That is, the conjugate acid of the electrogenerated base is oxidized to the base precursor and recycled as shown by Equation (4)

$$EGBH \xrightarrow{Oxidation} BP + H^+ \qquad (4)$$

It is apparent from Equation (4) that the reoxidation of the conjugate acid of the electrogenerated base to the base precursor will generate protons (or water), and it will be necessary to counteract the undesirable and deleterious effects of such species as shown in Equation (5).

$$H^+ + Scavenger \rightarrow Innocuous\ Scavenger\ Reaction\ Product \qquad (5)$$

This is especially necessary if the reoxidation is carried out in the preferred in situ manner as discussed hereinbelow.

The net effect of the general reactions of the present process as represented by Equations (1) through (5) are summarized as shown in Equation (6).

$$RH + CO_2 + Scavenger \rightarrow RCOO^- + Innocuous\ Scavenger\ Reaction\ Product \qquad (6)$$

It will be noted, however, that the applicants do not intend to be limited to any particular mechanism, as the demonstrated results are obtained regardless of the mechanism advanced in explanation thereof.

The base precursors which are generally suitable for use in the practice of the present invention are those which satisfy the following requirements:

(a) The base precursor must be more easily electroreducible than the carbon acid;

(b) The base precursor must be more easily electroreducible than carbon dioxide, for example, at less than −2.0 volts versus the saturated calomel electrode (mercury cathode);

(c) The base precursor must not be attacked nucleophilically by either the carbon acid anion or the electrogenerated base, that is, the base precursor must be sterically hindered at or near the site (or sites) where reduction will occur;

(d) The electrogenerated base generated from the base precursor must react with carbon dioxide either not at all, very slowly, or rapidly reversibly;

(e) The electrogenerated base generated from the base precursor must be a strong enough base to deprotonate the carbon acid; and (f) The base precursor must be easily regenerated from the conjungate acid of the electrogenerated base for reuse as a reactant.

Typical among the base precursors which generally satisfy requirements (a) through (f) hereinabove are ethenetetracarboxylate tetraesters and sterically hindered azobenzenes. Illustrative examples of the ethenetetracarboxylate tetraesters include tetraalkyl ethenetetracarboxylate esters such as, for example, tetramethyl ethenetetracarboxylate, tetraethyl ethenetetracarboxylate, tetra-n-propyl ethenetetracarboxylate, tetra-i-propyl ethenetetracarboxylate, tetra-n-butyl (and isomers thereof) ethenetetracarboxylate, tetra-n-pentyl (and isomers thereof) ethenetetracarboxylate, tetra-n-hexyl (and isomers thereof) ethenetetracarboxylate, tetra-n-heptyl (and isomers thereof) ethenetetracarboxylate, tetra-n-octyl (and isomers thereof) ethenetetracarboxylate, tetra-n-nonyl (and isomers thereof) ethenetetracarboxylate, tetra-n-decyl (and isomers thereof) ethenetetracarboxylate, and the like. Exemplary of the sterically hindered azobenzenes include 2,2'-di-t-butylazobenzenes, and the like, and 2,2',6,6'-tetrasubstituted azobenzenes, for example, 2,2',6,6'-tetraethylazobenzene, and the like. Of these base precursors, the tetraalkylethenetetracarboxylate esters are generally preferred because they are more readily available and/or more easily prepared. Moreover, they generally provide higher yields of the desired carboxylated carbon acid product in that they cannot be carboxylated irreversibly. It is recognized, however, that in certain instances the sterically hindered azobenzenes might be preferred as base precursors in view of the increased base strength of the electrogenerated bases generated therefrom.

Among the tetraalkyl ethenetetracarboxylate esters, those having alkyl group larger than methyl, such as, for example, tetraethyl ethenetetracarboxylate, tetra-n-butyl (and isomers thereof) ethenetetracarboxylate, tetra-n-hexyl (and isomers thereof) ethenetetracarboxylate, tetra-n-octyl (and isomers thereof) ethenetetracarboxylate, tetra-n-decyl (and isomers thereof) ethenetetracarboxylate, and the like are more preferred because so long as all other requirements are met, the larger the alkyl groups in the tetraalkyl ethenetetracarboxylate esters the more pronounced will be the tendency to minimize, or eliminate altogether, nucleophilic attack on the base precursor by either the carbon acid anion or the electrogenerated base. Among the tetraalkyl ethenetetracarboxylate esters having alkyl groups larger than methyl, the most preferred are those having alkyl groups containing from two (2) to four (4) carbon atoms, for example, tetraethyl ethenetetracarboxylate, tetra-n-propyl ethenetetracarboxylate, tetra-i-propyl ethenetetracarboxylate, and tetra-n-butyl (and isomers thereof) ethenetetracarboxylate because in general no additional advantage is offered by the tetraalkyl ethenetetracarboxylate esters having alkyl groups containing greater than four carbon atoms, that is, alkyl groups larger than butyl groups.

The term "and isomers thereof" following the names of various alkyl groups is employed herein to designate the isomers of the preceding alkyl group. For example, "and isomers thereof" following "tetra-n-butyl" designates isomeric butyl groups (other than n-butyl), such as i-butyl, s-butyl, and t-butyl. Thus the term "tetra-n-butyl (and isomers thereof) ethenetetracarboxylate" designates tetra-n-butyl ethenetetracarboxylate, tetra-i-butyl ethenetetracarboxylate, tetra-s-butyl ethenetetracarboxylate, and tetra-t-butyl ethenetetracarboxylate.

It will be noted that since there are four ester moieties contained in the ethenetetracarboxylate tetraesters as employed herein, the alkyl groups in the preferred tetraalkyl ethenetetracarboxylate esters can be the same or different; however, for practical reasons it is preferred that the alkyl groups contained in the four ester moieties be the same.

The carbon acids suitable for use in the present process must be strong enough to permit deprotonation by the electrogenerated base to form the carbon acid anion. In addition, the carbon acid anion ideally is a weak nucleophile, particularly toward the base precursor. Exemplary of the carbon acids which can be used in the practice of the present invention are N-alkyldiglycolimides, for example, N-methyldiglycolimide; dialkyl diglycolates, for example, diethyl diglycolate; 9-arylfluorenes, for example, 9-phenylfluorene; alkyl phenylacetates, for example, ethyl phenylacetate; alkyl acetates, for example, ethyl acetate; and the like. Of these, the N-alkyldiglycolimides are particularly important in that the N-alkyldiglycolimide-3-carboxylate contains, in addition to the added carboxyl group, an imide functionality whih can be hydrolyzed by conventional means. Thus, the N-alkyldiglycolimide-3-carboxylate can be converted to the corresponding methoxymethane-1,1,1'-tricarboxylate by hydrolysis. As a result of this step as well as conducting the electrolytic carboxylation of N-alkyldiglycolimides via electrogenerated bases in an anhydrous aprotic medium to produce N-alkyldiglycolimide-3-carboxylates, the present process provides an excellent route from the N-alkyldiglycolimides to the methoxymethane-1,1,1'-tricarboxylates. This is particularly important in that the alkali metal salts of such polycarboxylate ether compounds are excellent detergent builders.

As indicated hereinabove, the electrolysis of the present process is effected by passing a direct electric current through an anhydrous aprotic liquid electrolysis medium comprising the carbon acid, a base precursor, an anhydrous aprotic solvent, added carbon dioxide, and supporting electrolyte, which medium is in contact with a cathode. The medium must have sufficient conductivity to conduct the electric current. While media of less than ideal conductivity can be employed, it is preferred from an economic viewpoint not to have too high a resistance. The required conductivity is generally achieved by employing common supporting electrolytes, such as electrolyte salts whose cations have sufficiently negative discharge potentials, along with an anhydrous aprotic liquid solvent having a fairly good dielectric constant. In general, any combination of electrolyte and solvent can be employed which gives the desired conductivity and is sufficiently compatible with the starting materials and species generated therefrom to permit the carboxylation of the carbon acid to yield the desired carboxylated carbon acid. It is generally desirable to have the electrolyte, base precursor, carbon acid, and anhydrous aprotic solvent in a homogeneous solution. It will be noted, however, that many quaternary ammonium salt solutions may, in some respects, be dispersions rather than true solutions. In this regard, the present invention may use emulsions as well as true solutions so long as sufficient amounts of the base precursors (and the electrogenerated base generated therefrom), the carbon acid (and the carbon acid anion produced therefrom), and added carbon dioxide are dissolved or in solution so as to permit the desired carboxylation to occur.

The electrolytic carboxylation of carbon acids via electrogenerated bases of the present process must be carried out in scrupulously anhydrous media. This is necessary because water, a stronger acid than the carbon acids employed herein, would provide a source of more readily abstractable protons than that provided by the carbon acid. The presence of water, or for that matter any other source of similarly labile protons, would at worse effectively prevent altogether, or at best seriously impede the formation of the desired and necessary carbon acid anion, which ultimately is the species undergoing carboxylation to produce the desired carboxylated carbon acid. In other words, the electrolysis medium must not contain an acid stronger than the carbon acid to be carboxylated.

In the solvents employed in the present process it will generally be desirable to select a solvent (a) which is aprotic in nature; (b) which is a weaker carbon acid than the carbon acid to be carboxylated; (c) whose liquid range is such that ease of removal on product work-up is facilitated but loss by evaporation under process conditions is minimized; (d) which is relatively inert under process conditions; and (e) which has a sufficiently high dielectric constant in order to lower electrical resistance. It will be understood, however, that the choice and concentration of electrolyte can also be used to lower electrical resistance.

The term "relatively inert" is employed herein to describe solvents which, under process conditions, (a) do not preferentially undergo electrochemical reaction and (b) do not significantly react with either the starting materials, intermediates generated therefrom, or the desired final product (carboxylated carbon acid).

Solvents desirable for use in the practice of the present process have, in addition to characteristics (a) through (e) set forth hereinabove, low electrophilicity; that is, suitable solvents are substantially non-electrophilic. Further, it is found in practice that it is generally desirable to employ a solvent with a dielectric constant of at least 25, and preferably of at least 50. Examples of such anhydrous aprotic solvents include, for example, acetonitrile, propionitrile, dimethylformamide, N,N-dimethylacetamide, and the like.

In carrying out the present process, a supporting electrolyte is generally used to enhance conductivity, a "supporting electrolyte," as understood by those in the art, is an electrolyte capable of carrying electric current but not discharging under electrolysis conditions. In the present invention this primarily concerns discharge at the cathode, as the desired reaction occurs at the cathode. It will, of course, be recognized by those skilled in the art that, under certain conditions, discharge at the anode may also have a deleterious effect on the course of the reaction, product distribution, and overall product yield. The proper choice of a supporting electrolyte, however, is generally sufficient to either prevent any adverse effect as a result of the anodic discharge or to turn it to a useful advantage. In any event, the electrolyte employed will generally have cations of more negative discharge potential than the reduction potential of the base precursor used to generate the electrogenerated base. An electrolyte with a similar or slightly lower discharge potential than the reduction potential of the base precursor may be operative to some extent, but yields and current efficiency are adversely affected, so it is generally desirable to avoid any substantial discharge of the electrolyte salt during the electrolysis.

It will be recognized that discharge potentials will vary with cathode materials and their surface conditions, and various materials in the electrolysis medium. In order for the reaction to proceed, however, it is only necessary to have an effective reduction of the base precursor to generate the electrogenerated base under process conditions. Thus some electrolyte salts may be effective supporting electrolytes under process conditions even though nominally of less negative discharge potential than the base precursor employed.

In general, any supporting electrolyte salts can be utilized in carrying out the present process, with due consideration to having conditions suitable for discharge of the base precursor involved. The term "salt" is employed in its generally recognized sense to indicate a compound composed of a cation and an anion, such as produced by a reaction of an acid with a base. The electrolyte salts can be organic, inorganic, or mixtures of such, and composed of simple cations and anions or very large complex cations and anions.

Certain salts of alkali metals, amine and quaternary ammonium salts, or mixtures of such can be employed as supporting electrolytes. Among the alkali metal salts useful are lithium, sodium, and potassium salts, with sodium salts being generally preferred. Among the quaternary ammonium salts useful are the tetraalkylammonium, for example, tetramethylammonium, tetraethylammonium, tetra-n-propylammonium, and the like, heterocyclic and alkylarylammonium salts, for example, phenyltriethylammonium, and the like.

The term "quaternary ammonium" as employed herein has its usual recognized meaning of a cation having four organic groups substituted on the nitrogen.

Various anions can be used with the foregoing and other cations includng, for example, halides such as chloride, bromide, and iodide, perchlorates, tetrafluoroborates, hexafluorophosphates, sulfonates, tetraphenylborides, and the like. Aromatic sulfonates and similar anions, including those referred to as McKee salts, can be used, as can other hydrotropic salts, although the hydrotropic property may be of no particular significance when employed with anhydrous solvents or solvents having very low water content. Of the foregoing and other anions, the halides are preferred because of their ready availability and because of their ability to serve as convenient anodic depolarizers, particularly in undivided cells where otherwise the anode might adversely affect the reaction product of the halide anions; the bromide ion is particularly preferred because the molecular bromine generated therefrom by oxidation at the anode has the ability to oxidize the conjugate acid of the preferred electrogenerated bases, for example, tetraethyl ethane-1,1,2,2-tetracarboxylate, to the preferred base precursors, for example, tetraethyl ethenetetracarboxylate, while simultaneously exhibiting little, if any, tendency to adversely react with other components of the electrolysis medium, such as, for example, solvent, starting materials, and the like. This particular ability of molecular bromine is uniquely advantageous in that the base precursor need be employed in only catalytic amounts. Also, the source of the bromine is not of critical importance; it can be provided either as indicated hereinabove, by anodic oxidation of bromide ions, or by chemical means. Anodic oxidation, however, is preferred in that continuous operation is more easily effected and the possibility of product contamination by extraneous material is avoided.

The iodide ion, although suitable for use in the present process, is less preferred than the bromide ion because molecular iodine is not a sufficiently strong oxidizing agent to oxidize ethane-1,1,2,2-tetracarboxylate tetraesters, for example, tetraethyl ethane-1,1,2,2-tetracarboxylate to the ethenetetracarboxylate tetraester, for example, tetraethyl ethenetetracarboxylate. And since when iodide ion is employed ethane-1,1,-2,2-tetracarboxylate tetraesters are formed to some extent, even though substantially all the ethenetetracarboxylate tetraester is converted to the ethene-1,1,1,2,2-pentacarboxylate tetraester, which molecular iodine does oxidize to the ethenetetracarboxylate tetraester, a portion of the ethenetetracarboxylate tetraester is lost during each successive run. As a result, the preferred catalytic effect for the base precursor under process conditions is diminished. Moreover, the ethane-1,1,1,2,2-pentacarboxylate tetraester is insoluble in the electrolysis medium, thereby making more difficult continuous operation of the process.

The chloride ion is less preferred than the iodide ion because molecular chlorine generated therefrom reacts with the solvent to generate undesired protons as a by-product, unless a chlorine trap for example 1-hexene is employed to trap the molecular chlorine generated during the electrolysis, for example, as 1,2-dichlorohexane.

The term "chlorine trap" is employed herein to describe a compound capable of reacting with molecular chlorine to form innocuous products which have little or no adverse effect upon either the course of the reaction or upon product yield.

Thus the halide ions are preferred in the order of bromide ion > iodide ion > chloride ion.

The concentration of electrolyte salts is not narrowly critical. Thus, for example, suitable concentrations will often be in the range of about 1.0 percent to about 10 percent by weight of the electrolysis medium, or, on a molar basis, often in the range of about 0.001 to about 1.0 molar. The only limitation on the amount of electrolyte salt employed in that the amount is sufficient to promote efficient and economical operation and that it is soluble in the electrolysis medium. Thus electrolyte salts, for example, sodium chloride, which are incapable of being dissolved to any appreciable extent in the solvents of choice are generally not suitable for use in the practice of the present invention.

In regard to the solubility of the electrolyte salt in the electrolysis medium, it is important to note that certain preferred salts, for example, sodium bromide, are only slightly soluble in the solvents of choice in the present invention, for example, acetonitrile. When such difficultly soluble salts are employed, it is necessary to employ agents capable of inducing solubilization of such salts in the solvents of choice. Agents which are particularly useful for this purpose are compounds commonly known as crown ethers.

Crown compounds, in general, are macroheterocycles containing the repeating unit $(-Y-CH_2CH_2-)_n$ where Y may be a heteroatom, for example, oxygen, sulfur, nitrogen, or phosphorus. Of these, the most important are the crown ethers of the macrocyclic polyether class where Y is an oxygen. Thus these molecules in general contain repeating units $(-O-CH_2CH_2-)_n$ where n is equal to or greater than 2. Also, the ethylene units may be unsubstituted or substituted.

It will be recognized, however, that although crown compounds are defined as cycles, certain open-chain or acyclic compounds containing repeating units as defined hereinabove and having suitable stereochemistry for complexing alkali metal ions, while excluded in the formal sense, may behave very much like crown compounds and therefore similarly induce solubilization of the preferred salts in the solvents of choice, and in such cases can be used in the present invention as *psuedo* crown ethers. Such acyclic compounds include the polyglymes, for example, pentaglyme, hexaglyme, and the like.

For a general review of crown ether chemistry and the chemistry of related compounds, see Gokel et al, *Synthesis* 168–184 (1976), and references cited therein.

A crown ether suitable for use in the present process is 1,4,7,10,13,16-hexaoxacyclooctadecane, commonly known by its trivial name of 18-crown-6. Other crown ethers and *psuedo* crown ethers where n represents between about 5 and 20, with the ethylene units being either unsubstituted or substituted are also suitable for use in present process so long as they are capable of inducing solubilization of the difficultly soluble electrolyte salts and cause no adverse side effects.

Thus, a solution comprising an anhydrous aprotic solvent, an alkali metal bromide and a crown ether is a preferred solution which is suitable for conducting the electrolytic carboxylation of carbon acids via electrogenerated bases of the present process. Additionally, a quaternary ammonium bromide can, if desired, be added to the solution to increase its electric current-conducting capacity. It follows therefore that upon dissolving an N-alkyldiglycolimide, for example, N-methyldiglycolimide, or other carbon acid along with an ethenetetracarboxylate tetraester, for example, tetraethyl ethenetetracarboxylate, or other base precursor, and carbon dioxide in the solution, the passage of direct electric current at a cathode potential sufficient to effect reductive generation of the electrogenerated base will cause electrolytic carboxylation of the carbon acid according to the present process.

The concentration of the base precursor employed in the process of the present invention is not critical and limited only by the corresponding concentration of carbon acid employed. That is, sufficient amounts of base precursor must be employed so that the electrogenerated base generated therefrom will be present in sufficient amounts to deprotonate the available carbon acid to form the carbon acid anion. However, the total amount of base precursor needed to generate sufficient electrogenerated base for the desired deprotonation of the carbon acid present in the electrolysis medium need not actually be included in the electrolysis medium in that the base precursor can be recycled for reuse to generate additional electrogenerated base for continued deprotonation of the carbon acid. This is particularly true when the process is carried out in a continuous or semi-continuous mode--which involves a continuing series of batch preparations--of operation.

In any event, although concentrations as low as 0.01 percent by weight of the electrolysis medium can be employed, for reasons of efficiency and economy, it is preferred to employ concentrations from about 5.0 percent to about 25 percent by weight, or on a molar basis, from about 0.01 to about 0.05 molar, or even higher, of the base precursor.

Similarly, the preferred concentration of the carbon acid will often be in the range of about 5.0 percent to about 25 percent by weight of the electrolysis medium, or on a molar basis, from about 0.02 to about 0.05 molar, or even higher.

It will be noted, however, that the molar ratio of base precursor to carbon acid employed will depend in large measure upon the number of protons to be abstracted from the carbon acid and the number of active anionic sites on the electrogenerated base which are available for proton abstraction. For example, when the preferred base precursor tetraethyl ethenetetracarboxylate and the preferred carbon acid N-methyldiglycolimide are employed, the preferred molar ratio of base precursor to carbon acid is about 1:2 or greater.

As indicated hereinabove, it is advantageous to employ electrogenerated bases whose conjugate acids are capable of being easily oxidized to the corresponding base precursors. Under such circumstances and conditions the base precursor and the electrogenerated base derived therefrom will become involved as catalysts. In order to provide such a highly desirable effect, means must be provided for carrying out the desired oxidative conversion.

A number of options, including but not limited to those described hereinbelow, are available for converting the conjugate acid of the electrogenerated base to the base precursor for reuse as a reactant. The conjugate acid of the electrogenerated base can be (a) reoxidized by air outside the electrolysis cell (followed by drying of the base precursor prior to it being returned to the electrolysis cell); (b) oxidized directly or indirectly, with or without the assistance of air, in the anode compartment of a divided cell (in the presence of a scavenger to capture the protons (or water) generated so as to prevent migration into the catholyte); or (c) oxidized directly or indirectly, at the anode of an undivided cell (in the presence of a scavenger to capture the protons generated without generating water).

Since options (b) and (c) are, respectively, in situ methods of oxidizing the conjugate acid of the electrogenerated base in a divided cell and an undivided cell, they are the methods of choice.

It is apparent, however, that since protons (or water) will be generated while effecting the desired oxidation, and since the presence of protons in the electrolysis medium in any appreciable quantity would effectively prevent the required proton abstraction from the carbon acid by the electrogenerated base, appropriate and effective scavengers must be provided to capture any generated protons (without simultaneously generating water) so as to prevent subsequent deleterious reaction with the electrogenerated base. Scavengers suitable for use in the present process include, for example, alkali metal carbonates; alkali metal salts of very weak and very insoluble acids, for example, alkali metal tetraborates; basic alumina (which contains alkali metal aluminates, for example, sodium aluminates); and acidtype ion exchange resins in the alkali metal form, for example, sulfonic-acid-type ion exchange resins in the sodium form. Of these, the alkali metal carbonates are preferred, particularly as proton scavengers in that the non-acidic products produced therefrom are the innocuous alkali metal bicarbonates, for example, sodium bicarbonate. Moreover, since the sodium ion is the preferred cation among the alkali metal electrolyte salts, the use of sodium carbonate would provide a convenient source of sodium ions as well as minimize the possibility of obtaining mixtures of salts when the desired carboxylated carbon acid products are isolated as carboxylated carbon acid salts. Thus sodium carbonate is the preferred scavenger.

The term "scavenger" is employed herein to mean a compound or species which is capable of capturing protons (or water) to produce innocuous scavenger reaction products, or, more simply, innocuous products. These products are generally nonacidic, although they need not necessarily be such so long as they have little or no adverse effect either upon the course of the reaction or upon the product yield.

From the foregoing discussion, it is evident that ethane-1,1,2,2-tetracarboxylate tetraesters can be oxidized to ethenetetracarboxylate tetraester by contacting the ethane-1,1,2,2-tetracarboxylate tetraester, dissolved in an anhydrous aprotic solvent containing a scavenger capable of capturing protons, with molecular bromine. And as noted hereinabove, the source of the bromine is not of critical importance; it can be provided by anodic oxidation of bromide ions, or by chemical means.

In view of the discussion hereinabove, an exemplary method of conducting the present process can be described in the following manner. Reduction of an ethenetetracarboxylate tetraester, for example, tetraethyl ethenetetracarboxylate is carried out in the presence of a carbon acid, for example, N-methyldiglycolimide and carbon dioxide in acetonitrile containing tetraethylammonium bromide and sodium bromide solubilized by a crown ether, for example, 18-crown-6. Under such conditions both anionic sites in the "naked" dianion are utilized in proton abstraction according to Equation (7).

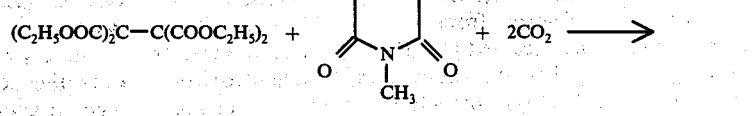

(7)

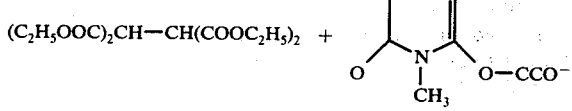

Equation (7) may be illustrated in further detail by Equations (8), (9), (10), and (11).

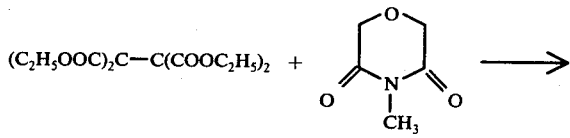 (8)

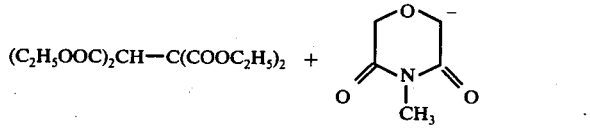

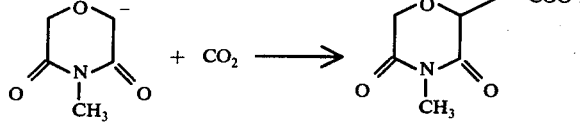 (9)

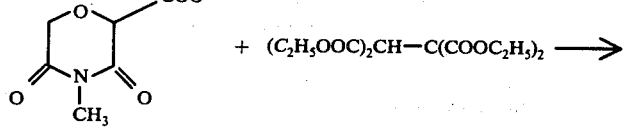 (10)

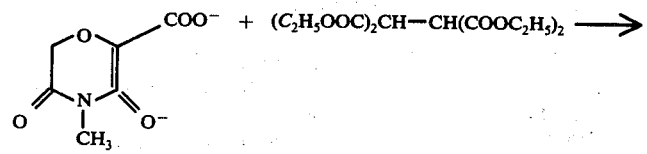

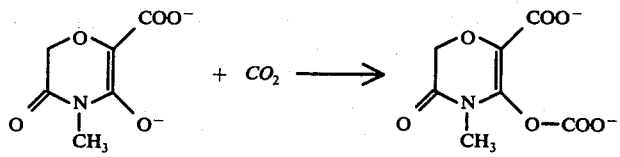 (11)

It is apparent from Equations (9) through (11) that when the N-methyldiglycolimide anion is allowed to react with added carbon dioxide, the dicarboxylate, 4-methyl-3,5-dioxo-6H,1,4-oxazine-2,O$^3$-dicarboxylate, is formed.

The anodic reaction ($2Br^- \rightarrow Br_2$) is utilized to regenerate tetraethyl ethenetetracarboxylate from tetraethyl ethane-1,1,2,2-tetracarboxylate according to Equation (12).

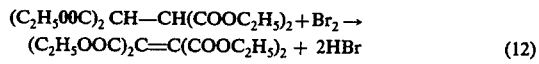 (12)

Sodium carbonate in the anolyte (when a divided cell is employed) serves both to remove hydrogen bromide and as a source of sodium ions. Thus, after electrolysis, the disodium 4-methyl-3,5-dioxo-6H,1,4-oxazine-2,O$^3$-dicarboxylate is filtered from the catholyte and the filtrate containing tetraethyl ethane-1,1,2,2-tetracarboxylate is charged to the anode compartment for regeneration of tetraethyl ethenetetracarboxylate in the subsequent reaction. The anolyte from the initial reaction, now containing tetraethyl ethenetetracarboxylate, is charged to the cathode compartment with additional N-methyldiglycolimide for carboxylation.

It will be noted that when sodium iodide, which is soluble in acetonitrile without added crown ether, is employed instead of the mixture of tetraethylammonium bromide and sodium bromide, only one of the anionic sites in substantially all the tetraethyl ethane-1,1,2,2-tetracarboxylate dianion is utilized for proton abstraction. Thus one of the anionic sites is available for reaction with carbon dioxide to yield the sodium tetraethyl ethane-1,1,1,2,2-pentacarboxylate, which precipitates in the catholyte along with the disodium 4-methyl-3,5-dioxo-6H,1,4-oxazine-2,O$^3$-dicarboxylate. The mixture is readily separated, however, by treatment with water.

Attention is drawn to the fact, however, that whatever the actual mechanistic pathway, whether both anionic sites or only one anionic site (in a dianionic electrogenerated base such as tetraethyl ethane-1,1,2,2- tetracarboxylate dianion) are utilized for proton abstraction, the present invention contemplates abstraction of at least one proton from the carbon acid by the electrogenerated base to form the carbon acid anion which subsequently undergoes carboxylation to yield the carboxylated carbon acid.

In general, the cathode potential can be maintained at a selected value or it can be varied. It will be apparent to those skilled in the art, however, that in order to minimize any possible adverse alteration in the course of the reaction or product distribution, the cathode potential is preferably no greater than that which is necessary to effect the desired generation of the electrogenerated base from the base precursor. That is, the cathode potential will be sufficiently negative to effect the desired reduction of the base precursor to the electrogenerated base but insufficiently negative to effect any undesired additional reduction of other components of the electrolysis medium, such as, for example, carbon dioxide. Suitable cathode potentials will often be no more than about −2.0 volts (versus the saturated calomel electrode) and usually no more than about −1.5 volts (versus the saturated calomel electrode). It will be recognized, however, that the value will vary with cathode materials and their surface conditions, and various materials in the electrolysis medium.

Various current densities can be employed in the present process. It will be desirable to employ high current densities in order to achieve high use of electrolysis cell capacity, and therefore for production purposes it will generally be desirable to use as high a density as feasible, taking into consideration sources and cost of electrical current, resistance of the electrolysis medium, heat dissipation, effect upon yields, and the like. Over broad ranges of current density, the density will not greatly affect the yield. Suitable ranges for efficient operation will generally be in the ranges from a few milliamperes per square centimeter of cathode surface, up to 10 or more milliamperes per square centimeter.

The present electrolysis can be conducted in the various types of cells known to the art. In general, such cells comprise a container made of material capable of resisting action of electrolytes, for example, glass or plastic, and one or more anodes and cathodes electrically connected to sources of direct electric current. The anode can be of any electrode material so long as it is relatively inert under reaction conditions. Anode materials suitable for use in the present process include, for example, platinum, palladium, graphite felt, graphite fibers, and the like.

Any suitable material can be employed as the cathode, various metals, alloys, graphite, and the like being known to the art. For example, mercury, platinum, lead, cadmium, copper amalgam, and graphite felt are suitable.

In the present process, either an undivided or a divided cell can be employed. A divided cell contains a suitable barrier material or separator which will prevent the free flow of reactants between the cathode and anode. Generally, the separator is some mechanical barrier which is relatively inert to electrolyte material, for example, a fritted glass filter, glass cloth, asbestos, porous poly(vinyl chloride), and the like. An ion exchange membrane can also be employed.

When a divided cell is used, it will be possible to employ the same electrolysis medium on both the cathode and anode sides, or to employ different media. Ordinarily, it will be desirable to employ the same electrolyte salt and solvent on both the cathode and anode sides; however, in some circumstances, it may be desirable to employ a different anolyte for economy of materials, lower electrical resistance, and the like.

As noted hereinabove, an undivided cell is also suitable for use in the present process. It will be appreciated that this could have advantages for industrial production in that electrical resistance across a cell divider is eliminated.

The electrolysis cells, whether divided or undivided, employed in the procedural Examples hereinbelow are primarily for laboratory demonstration purposes. Production cells are usually designed with a view to the economics of the process, and characteristically have large electrode surfaces, and short distances between electrodes.

For a general description of various laboratory scale cells, see Lund et al, "Practical Problems in Electrolysis," in *Organic Electrochemistry* (Baizer, ed.) Marcel Dekker, New York, 1973, pp. 165–249, and for some considerations of industrial cell designs, see Danly, "Industrial Electroorganic Chemistry," in Ibid, pp. 907–946.

The present process is suited to batch, semi-continuous, or continuous operations. Semi-continuous operations comprise:

(a) charging to the cathode compartment of a divided electrolysis cell a catholyte medium comprising a carbon acid, a base precursor, an anhydrous aprotic solvent, and added carbon dioxide;

(b) charging to the anode compartment of the divided electrolysis cell an anolyte medium comprising the conjugate acid of the electrogenerated base generated from the base precursor, the anhydrous aprotic solvent, supporting electrolyte, and scavenger;

(c) passing a direct electric current through the electrolysis cell to produce a carboxylated carbon acid and the conjugate acid of the electrogenerated base in the catholyte, and the base precursor and an innocuous scavenger reaction product in the anolyte;

(d) recovering the carboxylated carbon acid from the catholyte;

(e) removing the unreacted scavenger and the innocuous scavenger reaction product from the anolyte;

(f) charging to the anode compartment the catholyte from step (d) containing the conjugate acid of the electrogenerated base, with added scavenger.

(g) charging to the cathode compartment the anolyte from step (e) containing the base precursor, with added carbon acid; and (h) repeating steps (c) through (h).

Continuous operations can involve recirculation of a flowing electrolyte stream, or streams between the electrodes, with continuous or intermittent sampling of the stream for product removal. Similarly, additional reactants can be added continuously or intermittently, and electrolyte salt or other electrolyte components can be augmented, replenished, or removed as appropriate.

The temperature at which the process of the present invention is conducted is not critical. However, it may be desirable to avoid excessively high or elevated temperatures in that increased production of undesirable by-products may result. It may also be desirable to avoid elevated temperatures if volatile materials, for example, solvents, are utilized so that such materials will not escape, and various cooling means can be used for this purpose. Cooling to ambient temperatures is sufficient, but, if desired, temperatures down to 0° C or lower can be employed so long as the temperature is sufficient to permit the desired generation of the electrogenerated base followed by proton abstraction from the carbon acid and subsequent carboxylation of the carbon acid anion to occur. The amount of cooling capacity needed for the desired degree of control will depend upon the cell resistance and the electric current drawn. If desired, cooling can be effected by immersing the electrolysis cell in an ice or ice-salt bath or by permitting a component, such as the solvent, to reflux through a cooling condenser.

For convenience, temperatures in the range of about 0° C to about 100° C can be used, with temperatures between about 35° C and about 55° C being preferred.

The process of the present invention can be conducted at atmospheric pressure, superatmospheric pressures, and subatmospheric pressures. However, for reasons of economy and ease of construction of equipment employed in the present process, it is preferred to conduct this process at approximately atmospheric pressure.

The process of the present invention involves a carboxylation reaction, and therefore requires a source of the carboxyl group. Carbon dioxide admirably serves this purpose. The carbon dioxide can be supplied at atmospheric pressure or at a higher pressure, for example, 50 or 100 atmospheres or more of carbon dioxide. For reasons noted hereinabove, however, atmospheric pressures are generally preferred.

Other sources of the carboxyl group can also be employed in the present process. Various materials equivalent to or a source of carbon dioxide, for example, diethyl carbonate (as a source of the carbethoxy group), are suitable. The present invention contemplates reactions occurring in the presence of carbon dioxide (or its equivalent) regardless of its source.

The carboxylated carbon acid compounds obtained in the present process can be readily recovered by any of a number of well known procedures as the free carboxylic acids, salts, or esters thereof. It will be understood, however, that the isolation procedures employed in the procedural Examples and discussed hereinbelow are primarily for illustrative purposes. Other procedures can be employed, and may be preferred, for commercial use.

Upon completion of the electrolysis, the catholyte (when a divided cell is used) is evaporated in vacuo. The remaining residue is taken up in water and filtered to remove any undissolved solid material. Evaporation of the filtrate in vacuo yields the carboxylated carbon acid salt.

It will be noted, however, that if the carboxylated carbon acid salt or a precursor thereto (for example, disodium 4-methyl-5-oxo-6H,1,4-oxazine-2,$O^3$-dicarboxylate) is insoluble in the electrolysis medium, and therefore precipitates, the precipitate is collected by suction filtration, treated with water, and evaporated in vacuo to yield the desired carboxylated carbon acid salt.

Alternatively, the product is obtained as the corresponding free carboxylated carbon acid. An aqueous solution of the carboxylated carbon acid salt is mildly acidified with mineral acid, extracted with an appropriate solvent, for example, ethyl ether, dried over an appropriate dessicant, for example, magnesium sulfate, filtered, and evaporated in vacuo to yield the free carboxylated carbon acid.

A further alternative is to isolate the carboxylated carbon acid as the ester. The product, which exists as the carboxylic acid anion in solution, can be alkylated by treatment of the catholyte with an alkylating agent, for example, ethyl iodide or diethyl sulfate. The resulting mixture is filtered to remove undissolved materials. Evaporation of the filtrate to dryness and treatment of the residue with an appropriate solvent, for example, ethyl ether, filtering to remove undissolved materials, and removal of the solvent provides the ester.

It will be noted, however, that when, in addition to the carboxylic acid anion, other easily alkylated substituents, such as, for example, oxyanion groups or the equivalent thereof are present in the molecule, they too will undergo alkylation. And unless the polyalkylated compound is desired, it may be preferable in such instances to isolate the product as the free carboxylated carbon acid or the salt thereof.

It will be apparent, of course, that when diethyl carbonate (or, in general, any dialkyl carbonate) is used as the carboxylating agent, the corresponding ester is obtained directly and can be isolated as described hereinabove.

Similar isolation procedures are employed when an undivided cell is used.

The following examples illustrate the present invention and the manner by which it can be practiced.

EXAMPLE 1

A gas-tight, two-compartment H cell having a 100-milliliter cathode compartment and a 100-milliliter anode compartment was employed. The cathode and anode compartments were separated by a medium porosity glass frit. The cathode was a mercury pool (13 square centimeters surface area) in contact with a platinum wire sealed into the side near the bottom of the cathode compartment and the anode was a platinum mesh screen (6.25 square centimeters surface area). The cathode compartment was fitted with a 45/50 standard taper stopper having three 10/30 standard taper necks through which a saturated calomel reference electrode, a gas inlet tube for the passage of dry carbon dioxide, and a gas outlet tube were inserted. The anode compartment was similarly fitted with a 45/50 standard taper stopper through which a gas outlet tube and the anode lead connection were inserted. The outlet tubes were connected to paraffin-sealed gas bubblers and the anode lead connection was sealed into its inlet neck via a rubber septum. A magnetic stirrer located in each of the electrode compartments was used for stirring.

Procedure A — A mixture of 150 milliliters of dry acetonitrile (dried either by distillation from calcium hydride followed by filtration through a short column (6 inches × 1 inch; 15.24 centimeters × 2.54 centimeters) of active neutral alumina, or by successive filtrations through a 5-foot (152.4-centimeter) column of molecular sieves (Linde type 4A) and the above-described short column of active neutral alumina), 2.0 grams (0.0095 mole) of tetraethylammonium bromide, 4.0 grams (0.039 mole) of sodium bromide, and 2.0 grams (0.0076 mole) of 18-crown-6 (crown ether) was prepared and stirred overnight (approximately 16 hours), in a nitrogen-flushed dry box. A portion of the resulting solvent/electrolyte solution (75 milliliters), 3.16 grams (0.01 mole) of tetraethyl ethenetetracarboxylate, and 2.6 grams (0.02 mole) of N-methyldiglycolimide (4-methyl-3,5-dioxo-2H,6H,1,4-oxazine or 4-methyl-3,5-diketomorpholine) were charged to the cathode compartment. The remaining 75 milliliters of the solvent/electrolyte solution, 3.18 grams (0.01 mole) of tetraethyl ethane-1,1,2,2-tetracarboxylate, and 8.0 grams (0.075 mole) of sodium carbonate were charged to the anode compartment. The entire charging procedure was carried out in a nitrogen-flushed dry box. After the charging was complete, the cell was removed from the dry box and the electrolysis conducted at a temperature of 40°–45° C (water bath) and a cathode potential of −1.4 volts versus the saturated calomel electrode, with continuous passage of dry carbon dioxide through the catholyte. After a few minutes, a precipitate began to form in the catholyte. The initial current of 145 milliamperes descreased to 2 milliamperes over a 5.0-hour period. Upon completion of the electrolysis, the cell and its contents were transferred to the dry box and cooled to ambient temperatures. The precipitate in the catholyte was collected by suction filtration to yield 4.1 grams (78.8 percent) of the imidedicarboxylate disodium salt (disodium 4-methyl-5-oxo-6H,1,4-oxazine-2,$O^3$-dicarboxylate). Treatment of the disodium salt with water followed by evaporation in vacuo effected a quantitative conversion (3.07 grams) to the corresponding sodium N-methyl-diglycolimide-3-carboxylate (sodium 4-methyl-3,5-dioxo-2H,6H,1,4-oxazine-2-carboxylate or sodium 4-methyl-3,5-diketomorpholine-2-carboxylate.

Gas liquid chromatographic analysis of the catholyte filtrate showed the presence of tetraethyl ethane-1,1,2,2-tetracarboxylate and small amounts of unreacted N-methyl-diglycolimide starting material and 18-crown-6. Similar analysis of the anolyte filtrate (following removal of the sodium carbonate/sodium bicarbonate mixture by suction filtration) showed the presence of only tetraethyl ethenetetracarboxylate.

Procedure B — Employing the apparatus and procedure described in Procedure A above, the anolyte filtrate from Procedure A above and 2.6 grams (0.02 mole) of N-methyldiglycolimide were charged to the cathode compartment and the catholyte filtrate from Procedure A above and 8.0 grams (0.075 mole) of sodium carbonate were charged to the anode compartment. Electrolysis was carried out and, on completion, product isolation was effected as described in Procedure A above to yield 1.86 grams (48 percent) of sodium N-methyldiglycolimide-3-carboxylate.

The yield from repetitive runs averaged about 50 percent.

Gas liquid chromatographic analysis of the catholyte and anolyte filtrates following each run showed results similar to those obtained in Procedure A above.

EXAMPLE 2

An electrolysis apparatus similar to that described in EXAMPLE 1 above was employed except that the mercury pool cathode had a surface area of 10.7 square centimeters and the platinum mesh screen anode had a surface area of 5.3 square centimeters.

A solution of 2.0 grams (0.0019 mole) of sodium bromide, 2.0 grams (0.0076 mole of 18-crown-6, and 1.0 gram (0.0048 mole) of tetraethylammonium bromide in 150 milliliters of dry acetonitrile was prepared as described in Procedure A of EXAMPLE 1 above. Tetraethyl ethenetetracarboxylate (3.16 grams, 0.01 mole) and 4.36 grams (0.018 mole) of 9-phenylfluorene were dissolved in 75 milliliters of the solvent/electrolyte solution and charged to the cathode compartment. The anode compartment was charged with the remaining 75 milliliters of the solvent-electrolyte solution, 3.18 grams (0.01 mole) of tetraethyl ethane-1,1,2,2-tetracarboxylate, and 4.64 grams (0.04 mole) of sodium carbonate. The entire charging procedure was conducted in a nitrogen-flushed dry box. Electrolysis was carried out at a cathode potential of −1.2 volts versus the saturated calomel electrode at 40°–45° C in the presence of dry carbon dioxide, which was continuously passed through the catholyte during the electrolysis. After 4 hours, the initial current of 212 milliamperes decreased to 2 milliamperes. The sodium 9-phenylfluorene-9-carboxylate which precipitated in the catholyte was collected by filtration. The anolyte was mixed with 5.0 grams of active neutral alumina, stirred for one hour, and filtered to remove the sodium carbonate, sodium bicarbonate, and alumina solids. The anolyte filtrate, which contained tetraethyl ethenetetracarboxylate (base precursor), and 4.36 grams (0.018 mole) of 9-phenylfluorene were charged to the cathode compartment for carboxylation; the catholyte filtrate, which contained tetraethyl ethane-1,1,2,2-tetracarboxylate (conjugate acid of the electrogenerated base), and 4.64 grams (0.04 mole) of sodium carbonate was charged to the anode compartment for regeneration of tetraethyl ethenetetracarboxylate. Electrolysis was carried out and, on completion, product isolation and the anolyte-catholyte switch were repeated as described above. Electrolysis was carried out a third time. The sodium 9-phenylfluorene-9-carboxylate isolated in each of the three runs was treated with dilute hydrochloric acid at 0°–5° C. The cold aqueous mixture was extracted with chloroform, and the combined extracts were dried over anhydrous magnesium sulfate, filtered, and evaporated. The residues were dissolved in a minimum amount of a hot mixture of benzene and hexane (3:1) and the free acid, 9-phenylfluorene-9-carboxylic acid, crystallized and was collected by filtration, melting point 192°–196° C. Yields in the three sequential runs were, respectively, 4.17 grams, 81 percent; 3.81 grams, 74 percent; and 3.91 grams, 76 percent.

Gas liquid chromatographic analysis of the catholyte filtrate after each run showed the presence of tetraethyl ethane-1,1,2,2-tetracarboxylate and small amounts of unreacted 9-phenylfluorene and 18-crown-6.

Similar analysis of the anolyte filtrate showed the presence of 18-crown-6, and nearly quantitative regeneration of tetraethyl ethenetetracarboxylate.

EXAMPLE 3

A gas tight, two compartment H cell similar to that described in EXAMPLE 1 above was employed except that the cathode compartment had a 150 milliliter capacity, the anode compartment had a 50-milliliter capacity, the mercury pool cathode had a surface area of 28 square centimeters, the magnetic stirrers were removed, and that in the cathode compartment was replaced with a mechanical stirrer which necessitated a four-necked standard taper stopper. The stirrer shaft was sealed into the shaft inlet neck via a rubber septum.

The cathode compartment was charged with 100 milliliters of 0.3 molar tetraethylammonium chloride in dry dimethylformamide (dried by successive filtrations through a 5-foot (152.4 centimeter) column of 4A molecular sieves and a short column (6 inches × 1 inch; 15.24 centimeters × 2.54 centimeters) of active neutral alumina, 2.6 grams (0.02 mole) of N-methyldiglycolimide, and 1.6 grams (0.0051 mole) of tetraethyl ethenetetracarboxylate. The anode compartment was charged with 30 milliliters of the 0.3 molar tetraethylammonium chloride in dry dimethylformamide solution and 5 milliliters (3.4 grams, 0.04 mole) of 1-hexene to trap molecular chlorine generated during the electrolysis. The entire charging procedure was conducted in a nitrogen-flushed dry box. Following completion of the charging procedure, the cell was removed from the dry box and electrolysis was carried out at a temperature of 45°–50° C (water bath) and a cathode potential of −1.4 volts versus the saturated calomel electrode, with continuous passage of dry carbon dioxide through the catholyte. The initial current of 121 milliamperes fell to 0 milliamperes over a 1.6-hour period, at which time an additional 1.6 grams (0.0051 mole) of tetraethyl ethenetetracarboxylate was added to the catholyte. The current again rose to 121 milliamperes. When the current had decreased to 3 milliamperes, 10 milliliters (19.5 grams, 0.125 mole) of ethyl iodide was added to the catholyte and the reaction mixture stirred overnight (approximately 16 hours). The catholyte was separated from the mercury pool, filtered, and evaporated in vacuo to yield a solid residue which was triturated with ether (200 milliliters). The ethereal solution was filtered to remove undissolved solids, dried over anhydrous magnesium sulfate, and evaporated in vacuo. Vacuum fractional distillation of the residue yielded 0.3 gram of unreacted (N-methyldiglycolimide starting material and 3.9 grams (84.8 percent) of ethyl 3-ethoxy-4-methyl-5-oxo-6H,1,4-oxazine-2-carboxylate.

EXAMPLE 4

Employing the apparatus and procedure described in EXAMPLE 3 above, the cathode compartment was charged with 100 milliliters of 0.3 molar sodium iodide in dry acetonitrile (dried as described in Procedure A, EXAMPLE 1 above), 2.6 grams (0.02 mole) of N-methyldiglycolimide, and 3.2 grams (0.01 mole of tetraethyl ethenetetracarboxylate and the anode compartment was charged with 30 milliliters of the 0.3 molar sodium iodide in dry acetonitrile solution. Electrolysis was conducted as described in Procedure A, EXAMPLE 1 above for 4.2 hours. Upon completion of the electrolysis, the cell was transferred to the dry box and the catholyte, containing precipitated material, was separated from the mercury pool. The solvent was evaporated in vacuo to leave a residue which was mixed with water. Evolution of gas immediately ensued and a portion of the solid material dissolved. The undissolved solid was collected by suction filtration to give a quantitative yield of tetraethyl ethane-1,1,-2,2,-tetracarboxylate. Evaporation of the filtrate in vacuo yielded 2.03 grams (52 percent) of sodium N-methyldiglycolimide-3-carboxylate.

EXAMPLE 5

The electrolysis apparatus described in EXAMPLE 3 was employed.

Procedure A — The cathode compartment was charged with 100 milliliters of 0.2 molar tetraethylammonium iodide in dry dimethylformamide (dried as described in EXAMPLE 3 above), 9.84 grams (0.06 mole) of ethyl phenylacetate, and 8.56 grams (0.02 mole) of tetra-n-butyl ethenetetracarboxylate. The anode compartment was charged with 50 milliliters of the 0.2 molar tetraethylammonium iodide in dry dimethylformamide. The entire charging procedure was conducted in a nitrogen-flushed dry box. Following completion of the charging procedure, the cell was removed from the dry box and the electrolysis was carried out at a temperature of 45°–50° C (water bath) and a cathode potential of −1.3 volts versus the saturated calomel electrode, with continuous passage of dry carbon dioxide through the catholyte. The initial current of 210 milliamperes decreased to 2 milliamperes over a 4.2-hour period. Upon completion of the electrolysis, 10 milliliters (19.5 grams, 0.125 mole) of ethyl iodide was added to the catholyte and the reaction mixture stirred overnight (approximately 16 hours). The catholyte was separated from the mercury pool, filtered, and the solvent evaporated in vacuo to yield a residue which was triturated with 300 milliliters of ether. The ethereal solution was filtered to remove undissolved solid materials and evaporated in vacuo. Vacuum fractional distillation yielded 7.4 grams (78.4 percent based on the mole-equivalents of electrogenerated base available from tetra-n-butyl ethenetetracarboxylate) and unreacted ethyl phenylacetate starting material.

The residue remaining in the distillation vessel was dissolved in 50 milliliters of dry acetonitrile, treated with 3.2 grams (0.02 mole) of bromine, and stirred at 40° C for three hours. Quantitative gas liquid chromatographic analysis showed the mixture to contain 7.8 grams (92 percent) of tetra-n-butyl ethenetetracarboxylate.

Procedure B — 2-t-Butylnitrobenzene (30.0 grams, 0.17 mole) in 100 milliliters of ether was added to a suspension of 8.22 grams (0.22 mole) of lithium aluminum hydride in 700 milliliters of ether at a temperature of 5°–10° C. The mixture was allowed to come to ambient temperature and stirred for an additional 0.5-hour period. Hydrolysis was accomplished by the successive addition of 15 milliliters of water, 15 milliliters of 20 percent aqueous sodium hydroxide, and 30 milliliters of water. After mixing for 2 hours, the inorganic salts were removed by filtration and the ether evaporated. The residue was applied to an activated neutral alumina column (200 grams, 80–200 mesh) and eluted with hexane at a flow rate of 10 drops per minute. The initial fractions (about 700 milliliters) were discarded and the product, a bright red band on the column, was collected. Evaporation of the hexane followed by crystallization of the residue from ethanol gave 4.6 grams (18.7 percent) of 2,2′-di-t-butylazobenzene melting point, 90°–91° C.

An electrolysis apparatus similar to that described in EXAMPLE 3 above was employed except that the mercury pool cathode had a surface area of 32 square centimeters, the platinum screen anode had a surface area of 7 square centimeters, the 45/50 standard stopper contained an additional 10/30 standard taper neck to accommodate an addition funnel, and a plug of anhydrous neutral alumina (12.0 grams) was placed between the medium porosity frit and the cathode compartment. The cathode compartment was charged with 100 milliliters of 0.2 molar tetraethylammonium chloride in dry dimethylformamide (dried as described in EXAMPLE 3 above) and 10 milliliters (14.0 grams, 0.085 moles) of ethyl phenylacetate. The anode compartment was charged with 50 milliliters of the same solution (but without the ethyl phenylacetate) and 5 milliliters (3.4 grams, 0.04 mole) of 1-hexane to trap molecular chlorine generated during the electrolysis. The entire charging procedure was carried out in a nitrogen-flushed dry box. The cell was removed from the dry box and the electrolysis was carried out at a temperature of 40°–45° C (water bath) and a cathode potential of −1.9 volts versus the saturated calomel electrode, with continuous passage of dry carbon dioxide through the catholyte. After the passage of current had begun, a solution of 2.96 grams (0.01 mole) of 2,2′-di-t-butylazobenzene (from above) in 50 milliliters of 0.2 molar tetraethylammonium chloride in dry dimethylformamide was added dropwise to the catholyte at the rate of approximately 4 drops per minute (1 milliliter per 5 minutes). The current of 120–125 milliamperes obtained during the addition decreased rapidly to 2 milliamperes after the addition was complete (approximately 4 hours). Ethyl iodide (10 milliliters, 19.5 grams, 0.125 mole) was added to the catholyte and the mixture was stirred overnight (approximately 16 hours). The catholyte was separated from the mercury pool, poured into 300 milliliters of ice water, and extracted with two 150-milliliter portions of ether. The combined ethereal extracts were washed with five 100-milliliter portions of water, dried over anhydrous magnesium sulfate and evaporated in vacuo. Gas liquid chromatographic analysis of the residue showed the presence of diethyl phenylmalonate, 2,2′-di-t-butylazobenaene (regenerated by air oxidation during work-up), unreacted ethyl phenylacetate starting material, and an unidentified product. The product-containing residue was dissolved in hot ethanol and 2,2′-di-t-butylazobenzene crystallized and was removed by filtration. The filtrate was evaporated in vacuo and ethyl phenylacetate and diethyl phenylmalonate (3.5 grams, 74.2 percent based on the mole-equivalents of electrogenerated base available from 2,2′-di-t-butylazobenzene) were fractionated by vacuum distillation.

EXAMPLE 6

The electrolysis apparatus described in EXAMPLE 3 above was employed. A solution of 2.0 grams (0.019 mole) of sodium bromide, 2.0 grams (0.0076 mole) of 18-crown-6 (crown ether) and 1.0 gram (0.0048 mole) of tetraethylammonium bromide in 150 milliliters of dry acetonitrile was prepared as described in Procedure A, EXAMPLE 1 above. Tetraethyl ethenetetracarboxylate (3.16 grams, 0.01 mole) and 10.0 grams (0.11 mole) of ethyl acetate were dissolved in 100 milliliters of the solvent/electrolyte solution and charged to the cathode compartment. The remaining portion (50 milliliters) of the solvent/electrolyte solution was charged to the anode compartment. The entire charging procedure was carried out in a nitrogen-flushed dry box. The cell was removed from the dry box and electrolysis was conducted at a temperature of 45°–50° C (water bath) for 3.4 hours at a cathode potential of −1.2 volts versus the saturated calomel electrode, with continuous passage of dry carbon dioxide through the catholyte. The initial current of 250 milliamperes fell to 4 milliamperes over the electrolysis period. Ethyl iodide (10 milliliters, 19.5 grams, 0.125 mole) was added to the catholyte and the mixture stirred overnight (approximately 16 hours). Analysis by gas liquid chromatography showed diethyl malonate (15 percent based on the mole-equivalents of electrogenerated base available from tetraethyl ethenetetracarboxylate) and tetraethyl butane-1,1,2,2,-tetracarboxylate as products.

EXAMPLE 7

A 200-milliliter undivided, gas-tight cell was employed. The cathode was a mercury pool (38 square centimeters surface area) and the anode was a platinum mesh screen (10 square centimeters surface area). The cell was fitted with a 45/50 standard taper stopper having four 10/30 standard taper necks through which were inserted a gas inlet tube for the passage of dry carbon dioxide, a gas outlet tube, a water-cooled condenser, and the anode lead connection. The gas outlet tube and the water-cooled condenser were each connected to a paraffin-sealed gas bubbler and the anode lead connection was sealed into its inlet neck via a rubber septum. A magnetic stirrer was used for stirring. The anode, placed parallel to the surface to the mercury pool cathode, was located as close to its surface as possible without interfering with the operation of the magnetic stirrer.

The cell was charged in a nitrogn flushed dry box with 150 milliliters of a 0.3 molar solution of sodium iodide in dry acetonitrile (dried as described in Procedure A of Example 1 above), 5.2 grams (10.04 mole) of N-methyldiglycolimide (4-methyl-3,5-dioxo-2H,6H,1,4-oxazine or 4-methyl-3,5-diketomorpholine), 1.28 grams (0.0040 mole) of tetraethyl ethenetetracarboxylate, and 8.0 grams (0.075 mole) of sodium carbonate. The cell was removed from the dry box and connected to a source of dry carbon dioxide which was continuously passed through the electrolysis medium during the electrolysis. Electrolysis was conducted at a temperature of 45°–50° C (water bath) and a constant current of 0.8 amperes (800 milliamperes) for 12 hours. At the end of the electrolysis period, the electrolysis medium, which had darkened due to the accumulation of molecular iodine in the cell, was separated from the mercury pool and filtered to collect the disodium imidecarboxylate and sodium carbonate/sodium bicarbonate mixture. Nuclear magnetic resonance spectroscopic analysis of the solid showed the presence of 1.75 grams of the disodium imidedicarboxylate (disodium 4-methyl-5-oxo-6H, 1,4-oxazine-2,$O^3$-dicarboxylate).

Gas liquid chromatographic analysis of the filtrate showed the presence of tetraethyl ethane-1,1,2,2-tetracarboxylate, tetraethyl ethenetetracarboxylate, and unreacted N-methyldiglycolimide starting material.

The current efficiency was 15 percent, possibly due to the establishment of a molecular iodine-iodide equilibrium during the electrolysis.

EXAMPLE 8

To a stirred mixture of 3.18 grams (0.01 mole) of tetraethyl ethane-1,1,2,2-tetracarboxylate dissolved in 40 milliliters of anhydrous acetonitrile containing 2.12 grams (0.02 mole) of suspended sodium carbonate was added 1.6 grams (0.01 mole) of bromine under a nitrogen atmosphere. The mixture was stirred at 40° C for two hours, cooled to ambient temperatures, and filtered to remove undissolved solid material (sodium carbonate/sodium bicarbonate mixture). Gas liquid chromatographic analysis of the filtrate showed the presence of tetraethyl ethenetetracarboxylate in quantitative yield.

The carboxylated carbon acid products produced in the present process can be readily converted from salt to free acid or ester form, and the like. The carboxyl functionality makes the products suitable for various purposes in known manner as chemical intermediates. The products in various forms are suitable as detergent builders and can be modified for such purposes by formation of various esters or polyesters or others through reaction with glycols or other alcohols.

Many of the carboxylated carbon acid products contain, in addition to the added carboxyl group, certain functional groups which can be readily converted into other potentially valuable functionalities. For example, sodium N-methyldiglycolimide-3-carboxylate, being a cyclic imide, can be readily hydrolyzed by conventional means to the corresponding tricarboxylate. The alkali metal salts of this species, including for example, lithium, sodium, and potassium salts, particularly the sodium salt, are especially suitable as detergent builders.

While the invention has been described with respect to various specific examples and embodiments thereof, it will be understood that the invention is not limited thereto and that many alternatives, modifications, and variations will be apparent to those skilled in the art in light of the foregoing description. Accordingly, it is intended to embrace all such alternatives, modifications, and variations as fall within the spirit and broad scope of the invention.

What is claimed is:

1. A process for electrolytic carboxylation of carbon acids via electrogenerated bases, which process comprises subjecting an anhydrous aprotic liquid electrolysis medium comprising such carbon acid, a base precursor more easily electro-reducible than either the carbon acid or carbon dioxide, anhydrous aprotic solvent, added carbon dioxide, and supporting electrolyte to electrolysis at a cathode potential sufficiently negative to effect electro-reduction of the base precursor to the corresponding electrogenerated base but insufficiently negative to effect electro-reduction of either the carbon acid, added carbon dioxide, anhydrous aprotic solvent, or supporting electrolyte of the electrolysis medium, and thereafter recovering a carboxylated carbon acid.

2. The process of claim 1 wherein the base precursor is an ethenetetracarboxylate tetraester.

3. The process of claim 2 wherein the ethenetetracarboxylate tetraester is a tetraalkyl ethenetetracarboxylate.

4. The process of claim 3 wherein the tetraalkyl ethenetetracarboxylate is tetraethyl ethenetetracarboxylate.

5. The process of claim 3 wherein the tetraalkyl ethenetetracarboxylate is tetra-n-butyl ethenetetracarboxylate.

6. The process of claim 1 wherein the carbon acid is an N-alkyldiglycolimide and the carboxylated carbon acid is recovered as the carboxylated carbon acid salt.

7. The process of claim 6 wherein the N-alkyldiglycolimide is N-methyldiglycolimide and the carboxylated carbon acid salt is sodium N-methylglycolimide-3-carboxylate.

8. The process of claim 1 wherein the carbon acid is an N-alkyldiglycolimide and the carboxylated carbon acid is recovered as the carboxylated carbon acid ester.

9. The process of claim 8 wherein the N-alkyldiglycolimide is N-methyldiglycolimide and the carboxylated carbon acid ester is ethyl 3-ethoxy-4-methyl-5-oxo-6H,1,4-oxazine-2-carboxylate.

10. The process of claim 1 wherein the carbon acid is an alkyl acetate and the carboxylated carbon acid is recovered as the carboxylated carbon acid ester.

11. The process of claim 10 wherein the alkyl acetate is ethyl acetate and the carboxylated carbon acid ester is diethyl malonate.

12. The process of claim 1 wherein the anhydrous aprotic solvent is acetonitrile.

13. The process of claim 1 wherein the anhydrous aprotic solvent is dimethylformamide.

14. The process of claim 1 wherein the supporting electrolyte is an alkali metal halide.

15. The process of claim 14 wherein the alkali metal halide is sodium bromide.

16. The process of claim 1 wherein the supporting electrolyte is a quaternary ammonium salt.

17. The process of claim 16 wherein the quaternary ammonium salt is tetraethylammonium bromide.

18. The process of claim 16 wherein the quaternary ammonium salt is tetraethylammonium chloride.

19. The process of claim 1 wherein the supporting electrolyte is a mixture of an alkali metal halide and a quaternary ammonium salt.

20. The process of claim 19 wherein the supporting electrolyte is a mixture of sodium bromide and tetraethylammonium bromide.

21. The process of claim 1 wherein the electrolysis medium further comprises a crown ether.

22. The process of claim 21 wherein the crown ether is 18-crown-6.

23. The process of claim 1 wherein a mercury pool cathode and a platinum anode are used.

24. The process of claim 1 wherein the added carbon dioxide is continuously passed through the electrolysis medium during the electrolysis.

25. The process of claim 1 wherein the concentration of the carbon acid is between about 5.0 percent and about 25 percent by weight; the concentration of the base precursor is between about 0.50 percent and about 25 percent by weight; the concentration of the supporting electrolyte is between about 1.0 percent and about 10 percent by weight; and the electrolysis is conducted at temperatures between about 25° C and about 55° C.

26. The process of claim 1 wherein the cathode potential is no more than about $-2.0$ volts at mercury versus the saturated calomel electrode.

27. A process for conducting the electrolytic carboxylation of carbon acids in an anhydrous aprotic liquid electrolysis medium containing such carbon acid, a base precursor, an anhydrous aprotic solvent, added carbon dioxide, and supporting electrolyte, which process comprises:

(a) electrogenerating a base from the base precursor;

(b) allowing the electrogenerated base to react with the carbon acid to abstract at least one proton and produce a carbon acid anion and the conjugate acid of the electrogenerated base;

(c) allowing the carbon acid anion to react with the added carbon dioxide to form a carboxylated carbon acid; and (d) recovering the carboxylated carbon acid.

28. The process of claim 38 wherein the conjugate acid of the electrogenerated base is oxidized to the base precursor and recycled.

29. The process of claim 28 wherein the conjugate acid of the electrogenerated base is oxidized to the base precursor in the presence of a scavenger capable of capturing generated protons to produce innocuous scavenger reaction products.

30. The process of claim 29 wherein the scavenger is sodium carbonate and the innocuous scavenger reaction product produced therefrom is sodium bicarbonate.

31. A process for oxidation of ethane-1,1,2,2-tetracarboxylate tetraesters to ethenetetracarboxylate tetraesters, which comprises contacting the ethane-1,1,2,2-tetracarboxylate tetraester, dissolved in an anhydrous aprotic solvent containing a scavenger capable of capturing protons, with molecular bromine.

32. The process of preparing a methoxymethane-1,1,1'-tricarboxylate, which process comprises:
   (a) conducting the electrolytic carboxylation of an N-alkyldiglycolimide via an electrogenerated base in an anhydrous aprotic medium to produce an N-alkyldiglycolimide-3-carboxylate;
   (b) converting the N-alkyldiglycolimide-3-carboxylate to the methoxymethane-1,1,1'-tricarboxylate by hydrolysis; and
   (c) recovering the methoxymethane-1,1,1'-tricarboxylate.

33. A process for carboxylation of the N-methyldiglycolimide anion which comprises allowing the N-methyldiglycolimide anion to react with added carbon dioxide to form the 4-methyl-3,5-dioxo-6H,1,4-oxazine-2,$O^3$-dicarboxylate.

34. A solution suitable for conducting the electrolytic carboxylation of carbon acids via electrogenerated bases, which comprises an anhydrous aprotic solvent, an alkali metal bromide, and a crown ether.

35. The solution of claim 34 containing an N-alkyldiglycolimide as the carbon acid.

36. A solution suitable for conducting the electrolytic carboxylation of carbon acids in electrogenerated bases, which comprises an anhydrous aprotic solvent, a quaternary ammonium bromide, an alkali metal bromide, and a crown ether.

37. A solution comprising an anhydrous aprotic solvent, a quaternary ammonium bromide, an alkali metal bromide, a crown ether, and dissolved in the solution N-methyldiglycolimide, an ethenetetracarboxyklate tetraester, and carbon dioxide.

38. A semi-continuous electrolytic carboxylation of carbon acids via electrogenerated bases process which comprises:
   (a) charging to the cathode compartment of a divided electrolysis cell a catholyte medium comprising a carbon acid, a base precursor, an anhydrous aprotic solvent, and added carbon dioxide.
   (b) charging to the anode compartment of the divided electrolysis cell an anolyte medium comprising the conjugate acid of the electrogenerated base generated from the base precursor, the anhydrous aprotic solvent, supporting electrolyte, and a scavenger.
   (c) passing a direct electric current through the electrolysis cell to produce a carboxylated carbon acid and the conjugate acid of the electrogenerated base in the catholyte, and the base precursor and an innocuous scavenger reaction product in the anolyte;
   (d) recovering the carboxylated carbon acid from the catholyte;
   (e) removing the unreacted scavenger and the innocuous scavenger reaction product from the anolyte;
   (f) charging to the anode compartment the catholyte from step (d) containing the conjugate acid of the electrogenerated base, with added scavenger;
   (g) charging to the cathode compartment the anolyte from step (e) containing the base precursor, with added carbon acid; and
   (h) repeating steps (c) through (h).

* * * * *